United States Patent [19]

Burow, Jr. et al.

[11] 4,259,501
[45] Mar. 31, 1981

[54] METHOD FOR PREPARING 3-AMINO-5-(T-BUTYL)ISOXAZOLE

[75] Inventors: Kenneth W. Burow, Jr., Indianapolis; Richard F. Eizember, Greenwood, both of Ind.

[73] Assignee: Eli Lilly and Company, Indianapolis, Ind.

[21] Appl. No.: 967,342

[22] Filed: Dec. 7, 1978

Related U.S. Application Data

[63] Continuation-in-part of Ser. No. 880,266, Feb. 22, 1978, abandoned.

[51] Int. Cl.$^3$ ............................................. C07D 261/06
[52] U.S. Cl. ....................................................... 548/246
[58] Field of Search ...................... 260/307 H; 548/246

[56] References Cited

U.S. PATENT DOCUMENTS 3,435,047  3/1969  Iwai ........................................ 260/307
4,062,861 12/1977  Yukimaga ........................... 260/307 H

FOREIGN PATENT DOCUMENTS 818161 11/1974 Belgium .
2819264 11/1978 Fed. Rep. of Germany .
37-1161665 12/1962 Japan .

OTHER PUBLICATIONS

Wahlberg, Ber. 65 B, 1857–1864 (1932).

Primary Examiner—Nicholas S. Rizzo
Assistant Examiner—Lisa Jones
Attorney, Agent, or Firm—Karen B. O'Connor; Dwight E. Morrison; Arthur R. Whale

[57] ABSTRACT

3-Amino-5-(t-butyl)isoxazole, in optimum yield, is prepared in a stepwise manner by reacting a lower alkyl pivalate and acetonitrile in the presence of a base to yield pivalyl acetonitrile, which in turn is allowed to react with hydroxylamine under controlled conditions of pH to yield the desired compound. The compound is a useful intermediate for the preparation of isoxazole derivatives having utility as herbicides.

13 Claims, No Drawings

METHOD FOR PREPARING 3-AMINO-5-(T-BUTYL)ISOXAZOLE

CROSS-REFERENCE

This application is a continuation-in-part of co-pending U.S. application Ser. No. 880,266, filed Feb. 22, 1978, now abandoned.

BACKGROUND OF THE INVENTION

1. Field of the Invention

This invention relates to the preparation of an isoxazole. More particularly this invention relates to a method of optimizing the yield of 3-amino-5-(t-butyl)isoxazole over the yield of the isomeric 5-amino-3-(t-butyl)isoxazole. The 3-amino-5-(t-butyl)isoxazole is useful as an intermediate in the preparation of isoxazole derivatives having utility as herbicides.

There is a continuing need in agriculture for effective herbicides both for broad spectrum and selective use, and it is important to be able to synthesize these needed herbicides.

2. Description of the Prior Art

In the prior art U.S. Pat. No. 3,435,047 (Mar. 25, 1969), teaches a process for preparing 3-aminoisoxazole derivatives. The therein disclosed method involves reacting propiolonitriles with hydroxylamine in the presence of an alkali metal hydroxide.

Also in the prior art is Wahlberg, Ber. 65B, 1857–64 (1932), C. A. 27, 957$^3$ (1933), wherein is disclosed the preparation of 3-tert-butyl-5-imino-4,5-dihydroisoxazole from pivalyl acetonitrile in acetic acid as the solvent, in reaction with the calculated amount of hydroxylamine hydrochloride and sodium acetate.

Another prior art reference is Japanese Pat. No. 11616/65 (Derwent Basic No. 17,246), which is directed to a process for converting 3-carbamoyl-5-alkyl isoxazole to 3-amino-5-alkyl isoxazole by the Hoffmann reaction.

Yet another prior art reference is U.S. Pat. No. 4,062,861 (Dec. 13, 1977), the U.S. counterpart of Belgian Pat. No. 818,161 (Derwent No. 00128W/01), which is directed to herbicidal isoxazolylurea derivatives. Among the starting materials utilized in preparing the compounds disclosed and claimed in this reference is 3-amino-5-(t-butyl)isoxazole. However, there is no teaching in this reference of the method of preparing this starting material.

SUMMARY OF THE INVENTION

This invention relates to a method for optimizing the yield of 3-amino-5-(t-butyl)isoxazole over the yield of the isomeric 5-amino-3-(t-butyl)isoxazole. The method is carried out in a stepwise manner utilizing in a first step the reaction of a lower alkyl pivalate with acetonitrile in the presence of a base to yield pivalyl acetonitrile, which pivalyl acetonitrile is then reacted with hydroxylamine under carefully controlled conditions of pH to yield a preponderance of 3-amino-5-(t-butyl)isoxazole.

DESCRIPTION OF THE INVENTION

The method disclosed herein provides an optimum yield of the desired 3-amino-5-(t-butyl)isoxazole. The method is carried out stepwise.

In the first step, a lower alkyl ester of pivalic acid, suitably methyl pivalate, is allowed to react with acetonitrile in the presence of a base, such as sodium hydride, in the presence of a solvent under an atmosphere of nitrogen at the reflux temperature of the reaction mixture for a time sufficient to bring about substantial completion of the reaction. Other bases which can be used in the reaction include sodium ethoxide and sodium methoxide. Suitable solvents include tetrahydrofuran, ether, toluene, ethanol and methanol. While substantial completion of the reaction occurs in about 7 hours, longer times of reflux, for example, up to about 24 hours, can be employed. At the end of the reaction time, the reaction mixture is concentrated in vacuo to remove the solvent, water is added, and the aqueous mixture made acid with, for example, aqueous hydrochloric acid. The desired product, the pivalyl acetonitrile, precipitates from the acid solution and is filtered off and dried.

The second step of the synthesis of 3-amino-5-(t-butyl)isoxazole is carried out by allowing the pivalyl acetonitrile, prepared as described hereinabove, to react with hydroxylamine under carefully controlled conditions of pH, in a suitable solvent at a suitable temperature for a period of time such that substantially complete reaction is obtained to form the preferred 3-amino-5-(t-butyl)isoxazole. In one embodiment the hydroxylamine is used in salt form, for example, hydroxylamine hydrochloride, and the hydroxylamine salt is added to a mixture of the pivalyl acetonitrile and base in the solvent, and the pH is adjusted to the preferred range. Temperatures of from about 0° C. to about the reflux temperature of the reaction mixture can be employed, with the preferred reaction temperatures ranging from about room temperature to about the refluxing temperature of the reaction mixture. Reaction times of course vary inversely with the reaction temperature, i.e., from about 3 days to about 1 hour. Thus, reaction times at the reflux temperature of the reaction mixture come within the range of from about 1 hour to about 24 hours, preferably from about 7 hours to about 22 hours, with the latter range of reaction time providing generally optimum yields of the desired 3-amino-5-(t-butyl)isoxazole. Suitable solvents include mixtures of an alcohol and water, such as ethanol-water, methanol-water, ethylene glycol-water, isopropanol-water, and n-butanol-water. The optimum solvent system is composed of ethanol and water, with ratios of from about 95:5 to 42:58 ethanol:water, all providing acceptable yields of the 3-amino isomer.

While hydroxylamine hydrochloride is the salt form of choice, hydroxylamine sulfate also can be used, albeit less favorable product isomer ratios appear to be obtained. Suitable bases include sodium hydroxide, lithium hydroxide, potassium hydroxide, calcium hydroxide, sodium carbonate, sodium bicarbonate, and potassium carbonate. The preferred base is selected from the group consisting of sodium hydroxide, lithium hydroxide, and potassium hydroxide.

In adding the hydroxylamine hydrochloride to the reaction mixture, it appears that a quick addition is preferable. Best results appear to be obtained by adding an aqueous solution of the hydroxylamine hydrochloride to the basic solution of the pivalyl acetonitrile, and then, within the first 15 to 30 minutes, adjusting the pH to within the range of from about 5.0 to about 8.0, preferably from about 6.0 to about 7.0, with the pH range of choice being pH about 6.2 to about 6.5. This careful control of the pH of the reaction mixture is important in order to obtain the maximum yield of the 3-amino-5-(t-butyl)isoxazole since the reaction is very sensitive to the pH. A pH lower than about 5.0 results in the formation of an isoxazolone compound as the principal product. Higher pH values, that is, above about pH 8.0, result in unacceptably large amounts of the 5-amino-3-(t-butyl-)isoxazole, compared to the amount of the desired 3-amino-5-(t-butyl)isoxazole. Even at pH 7.0, the ratio of the desired 3-amino compound to the 5-amino compound is less desirable.

This careful control of the pH is important, as explained above, and should extend over about the first 6 hours of the reaction time between the hydroxylamine and the pivalyl acetonitrile.

Alternatively, the second step of the synthesis of 3-amino-5-(t-butyl)isoxazole can be carried out using the hydroxylamine free base. Thus, for example, a solution of the hydroxylamine salt in water is prepared and is adjusted to a neutral pH by addition of base, for example, aqueous sodium hydroxide. This neutral solution of hydroxylamine is then added to the neutral solution of the pivalyl acetonitrile. Following the addition, the pH of the reaction mixture is then carefully controlled within the limits set forth above. Such control should extend over the first approximately 6 hours of the reaction time in order to obtain the optimum yield of the 3-amino isomer.

In working up the reaction mixture, the most effective procedure presently known is to allow the crystallization of the 3-amino isomer to occur after the solvent is removed in vacuo without applying heat. Although it is possible to obtain the 3-amino isomer from the reaction mixture by changing the pH, or forcing the crystallization with colder temperatures, or by the addition of sodium chloride, such measures appear to yield the desired 3-amino-5-(t-butyl)isoxazole in a less pure form.

That the invention may be more fully understood, the following examples further illustrate the novel method.

EXAMPLE 1

Preparation of pivalyl acetonitrile

In a 1 l. flask under an atmosphere of dry nitrogen there was placed 26.4 g. of a 50% oil dispersion of sodium hydride together with 240 ml. of dry tetrahydrofuran. While this mixture was refluxed there was added thereto dropwise over a period of about 1 hour a mixture of 40.6 g. of methyl pivalate and 22.6 g. of acetonitrile in 40 ml. of dry tetrahydrofuran. When addition was complete, the mixture was refluxed overnight. The reaction mixture was worked up by evaporating part of the tetrahydrofuran in vacuo and dissolving the remaining solution in about 300 ml. of water. This aqueous mixture was acidified to about pH 4 using concentrated aqueous hydrochloric acid. The remainder of the tetrahydrofuran was then removed using a rotovapor. The solid which was formed was filtered and slurried with 150 ml. of hexane to remove mineral oil. The crystals were filtered and dried. The crystals had a melting point of about 57°–59° C. and were identified as pivalyl acetonitrile. Yield: 36.3 g. (83%).

EXAMPLE 2

Preparation of 3-amino-5-(t-butyl)isoxazole

In a 1 l. 3-neck round bottom flask there was placed 30 g. of pivalyl acetonitrile, 13.5 g. of lithium hydroxide, 394 ml. of water and 281 ml. of ethanol. This mixture was heated to reflux and there was added thereto over a period of 10 minutes 94 ml. of an aqueous solution of 22.2 g. of hydroxylamine hydrochloride. The pH of the reaction mixture after the addition was complete was about 7.3. This pH was adjusted to about pH 6.7 using concentrated aqueous hydrochloric acid. After 30 minutes the pH was about 6.1. After 1 hour the pH was about 6.3. The pH was checked again at 2 hours and at 3 hours after the addition was complete and the pH at those times was about 6.6. A recheck of the pH at 4 hours, 5 hours, and 6 hours revealed the pH to be at about 6.7. The reaction mixture was then refluxed overnight. The following morning the pH was about 6.8. The reaction mixture was cooled and the ethanol removed from the mixture on the rotovapor at room temperature. A solid which separated was filtered off and dried. It weighed 18.65 g. and it was determined by vpc that the product contained 97% of the desired 3-amino-5-(t-butyl)isoxazole, and 1.6% of 5-amino-3-(t-butyl)isoxazole. Yield: 52% of desired isomer.

EXAMPLE 3

Preparation of 3-amino-5-(t-butyl)isoxazole

In this preparation sodium hydroxide was used as the base in place of lithium hydroxide.

In a 1 l. round bottom 3-neck flask there was placed 30 g. of pivalyl acetonitrile, 12.8 g. of sodium hydroxide, 394 ml. of water, and 281 ml. of ethanol. This mixture was heated to refluxing and there was added thereto over a period of about 10 minutes an aqueous solution of 22.2 g. of hydroxylamine hydrochloride. The pH of the reaction mixture after addition was complete was about 6.4. After 30 minutes the pH was determined to be about 6.5. After 1½ hours the pH was about 6.8, and after 2 hours the pH was about 7.0. The pH was adjusted to about 6.2 using concentrated aqueous hydrochloric acid. After another 3 hours the pH was about 6.6. The reaction mixture was refluxed overnight and at the end of 22 hours of reaction time the pH was about 7.3. The reaction mixture was cooled and ethanol removed in vacuo. The solid which separated was filtered off and dried. It weighed 18.9 g., had a melting point of about 103°–105° C., and was determined by vpc to contain 91.2% of 3-amino-5-(t-butyl)isoxazole and 5.2% of 5-amino-3-(t-butyl)isoxazole. Yield: 56% of desired isomer.

EXAMPLE 4

Preparation of 3-amino-5-(t-butyl)isoxazole

In a 100 ml. round bottom flask there was placed 2 g. of pivalyl acetonitrile, 0.64 g. of sodium hydroxide, 35 ml. of water, and 25 ml. of ethanol. This mixture was heated to reflux and the pH was determined to be about 8.9. Then an aqueous solution of 1.0 g. of hydroxylamine hydrochloride was slowly added. At the end of the addition the pH was about 6.3. The pH of the reaction mixture was adjusted to about 6.5. After 1 hour, the pH was about 6.3 and was again adjusted to about 6.5. After 2 hours the pH was observed to be about 7.0 and was again adjusted to pH about 6.5. At 3 hours and again at 4 hours, the pH was determined to be about 6.5. The reaction mixture was allowed to reflux overnight and the following morning the pH was determined to be about 6.1. The ethanol was removed using a rotovapor and a yellow solid precipitated. This solid was filtered off and dried. It weighed 1.1 g. and it was determined by vpc to contain 94.2% of 3-amino-5-(t-butyl)isoxazole and 3.7% of 5-amino-3-(t-butyl)isoxazole. The product had a melting point of about 103°–105° C. Yield: 73.6% of desired isomer.

EXAMPLE 5

Preparation of 3-amino-5-(t-butyl)isoxazole

In a 100 ml. round bottom flask there was placed 2 g. of pivalyl acetonitrile, 0.64 g. of sodium hydroxide, 35 ml. of water, and 25 ml. of ethanol. This mixture was heated to reflux. The pH of the mixture was determined to be about 8.6. Then 1.1 g. of hydroxylamine hydrochloride in 15 ml. of water was added dropwise. At the end of the addition the pH of the reaction mixture was about 5.1. The pH of the reaction mixture was adjusted to about 7.0. After 1 hour the pH was determined to be about 7.6 and was adjusted back to about 7.0. After 2 hours the pH was determined to be about 6.9 and was readjusted to about 7.0. After 3 hours the pH was determined to be about 7.5 and was adjusted to about 7.0. After 4 hours the pH was determined to be about 6.8 and was readjusted to about 7.0. The reaction mixture was allowed to reflux overnight and the following morning the pH was determined to be about 6.3 and was readjusted to about 7.0. The ethanol solvent was stripped using a rotovapor and a yellow solid precipitated. The solid was filtered off and dried. The solid weighed 1.1 g. and had a melting point of about 101°–104° C. It was determined by vpc to contain 92.6% of 3-amino-5-(t-butyl)isoxazole and 4% of 5-amino-3-(t-butyl)isoxazole. Yield: 72.9% of desired isomer.

EXAMPLE 6

Preparation of 3-amino-5-(t-butyl)isoxazole

In a 100 ml. round bottom flask there was placed 2 g. of pivalyl acetonitrile, 0.64 g. of sodium hydroxide, 17.5 ml. of water and 12.5 ml. of ethanol. This mixture was heated to refluxing and a aqueous solution of 1.1 g. of hydroxylamine hydrochloride was added dropwise. When addition was complete the pH of the mixture was about 7.2. This was adjusted to pH about 6.3 using 10% aqueous hydrochloric acid. After 1 hour the pH was about 7.0 and was adjusted with 10% HCl to pH about 6.5. At the end of 2 hours the pH was about 6.8. At the end of 3 hours the pH was about 6.9. At 3½ hours the pH was about 6.5. The reaction mixture was refluxed overnight and the following morning the pH was about 6.8. The reaction mixture was concentrated using the rotovapor and the solid material which precipitated was filtered off and dried. It weighed 1.3 g., had a melting point of about 103°–104° C., and was determined by vpc to contain 90.68% of 3-amino-5-(t-butyl)-isoxazole and 6.68% of 5-amino-3-(t-butyl)isoxazole. Yield: 65.9% of desired isomer.

EXAMPLE 7

Preparation of 3-amino-5-(t-butyl)isoxazole

In a 100 ml. round bottom 3-neck flask there was placed 2 g. of pivalyl acetonitrile, 25 ml. of ethanol, and 10 ml. of water. While this mixture was refluxed, a solution of 0.89 g. of lithium hydroxide and 1.5 g. of hydroxylamine hydrochloride in 25 ml. of water was added. At the end of the addition, the pH of the reaction mixture was about 7.2. The pH was adjusted to about 6.8 using concentrated aqueous hydrochloric acid. After 30 minutes the pH was about 6.0 and was readjusted to about 6.5 using an aqueous solution of lithium hydroxide. After 1 hour the pH was about 6.2 and was adjusted to about 6.8 using an aqueous solution of lithium hydroxide. At 1.5 hours the pH was about 6.6. At 2 hours the pH was about 6.7. At 2½ hours the pH was about 6.8. At 3 hours the pH was about 7.0 and was adjusted to about 6.5 using concentrated aqueous hydrochloric acid. After 20 hours the pH was about 7.0. The reaction mixture was cooled and the ethanol stripped on the rotovapor. The solid which precipitated was filtered off and dried. It weighed 1.4 g., had a melting point of about 105°–106° C., and was determined by vpc to contain 98.5% of 3-amino-5-(t-butyl)isoxazole and 1% of 5-amino-3-(t-butyl)isoxazole. Yield: 62.5% of desired isomer.

EXAMPLE 8

Preparation of 3-amino-5-(t-butyl)isoxazole

In a 100 ml. round bottom 3-neck flask was placed 2 g. of pivalyl acetonitrile, 0.64 g. of sodium hydroxide, 35 ml. of water and 12.5 ml. of ethanol. This mixture was heated to reflux and an aqueous solution of 1.1 g. of hydroxylamine hydrochloride was added. The pH at the end of the addition was about 6.0. After 1 hour the pH was determined to be about 6.3. After 2 hours the pH was determined to be about 6.7. After 3 hours the pH was determined to be about 6.5. The following morning after the reaction mixture had refluxed overnight the pH was about 7.2. The ethanol was removed in vacuo using the rotovapor. The solid which separated was filtered off and dried. It had a melting point of 105°–106° C., and weighed 1.1 g. It was determined by vpc that the product contained 92.49% of 3-amino-5-(t-butyl)isoxazole and 4.67% of 5-amino-3-(t-butyl)isoxazole. Yield: 60.7% of desired isomer.

EXAMPLE 9

Preparation of 3-amino-5-(t-butyl)isoxazole

In a 100 ml. round bottom 3-neck flask there was placed 2 g. of pivalyl acetonitrile, 0.9 g. of potassium hydroxide, 25 ml. of ethanol, and 35 ml. of water. The mixture was heated to refluxing, and an aqueous solution of hydroxylamine hydrochloride was added. After the addition was complete, the mixture showed a pH of 5.6. The pH was immediately adjusted to 6.2 by adding aqueous saturated sodium bicarbonate solution. The pH of the reaction mixture after 1 hour was 6.3. After 2 hours, the pH of the reaction mixture was 6.4. After 3 hours, the pH of the reaction mixture was 6.5. The reaction mixture was allowed to reflux overnight, and the following morning the pH was 6.8. The reaction mixture was cooled and the ethanol stripped on the rotovapor. The white solid which separated was filtered off and dried. The solid weighed 0.8 g., and was determined by vpc to contain 91.9% 3-amino-5-(t-butyl)isoxazole and 5.7% of 5-amino-3-(t-butyl)isoxazole. Yield of desired isomer was 48%.

EXAMPLE 10

Preparation of 3-amino-5-(t-butyl)isoxazole

In a 100 ml. round bottom 3-neck flask was placed 2 g. of pivalyl acetonitrile in 25 ml. of ethanol. To this mixture a solution of 1.1 g. of hydroxylamine hydrochloride in 15 ml. of water was added quickly. The pH of the reaction mixture was adjusted to pH 7, using aqueous 10% sodium bicarbonate solution, and heated to refluxing. After 1 hour the pH was 8.5, and was adjusted to pH 7, using concentrated aqueous hydrochloric acid. After 2 hours, the pH was 8.5, and was again adjusted to pH 7. After 3 hours, the pH was 8.0, and was adjusted to pH 6.7. Refluxing of the reaction mixture was continued overnight. The next morning, the pH was 7.2, and was adjusted to pH 7. The reaction mixture was cooled and the ethanol stripped on the rotovapor. The remaining mixture was filtered and the solid thereby obtained dried. The solid has a melting point of about 105°–106° C., and weighed 0.7 g. This solid was determined by vpc to contain 93% of 3-amino-5-(t-butyl)isoxazole and 5.6% of 5-amino-3-(t-butyl)isoxazole. The yield of desired isomer was 31%.

We claim:

1. A method for preparing 3-amino-5-(t-butyl)-isoxazole, which comprises:

Step I, reacting an alkyl pivalate with acetonitrile in the presence of a base, to yield pivalyl acetonitrile, and Step II, reacting pivalyl acetonitrile with hydroxylamine in a solvent at a temperature in the range of from about room temperature to about the reflux temperature of the reaction mixture at a pH range of from about pH 6.0 to about pH 7.0.

2. The method of claim 1 wherein in Step I the base is sodium hydride.

3. The method of claim 1 wherein Step I is carried out in tetrahydrofuran.

4. The method of claim 1 wherein Step II is carried out in ethanol/water as the solvent.

5. The method of claim 1 wherein Step II is carried out at a pH of from about pH 6.2 to about pH 6.5.

6. A method for preparing 3-amino-5-(t-butyl)-isoxazole which comprises adding a hydroxylamine salt to a mixture of pivalyl acetonitrile and a base in a solvent at a temperature in the range of from about room temperature to about the reflux temperature of the reaction mixture, adjusting and maintaining the pH of the resulting mixture at a pH range of from about pH 6.0 to about pH 7.0, refluxing the mixture for from about 1 to about 24 hours, and isolating the product.

7. The method of claim 6 wherein the base is lithium hydroxide.

8. The method of claim 6 wherein the base is sodium hydroxide.

9. The method of claim 6 wherein the solvent is ethanol/water.

10. The method of claim 6 wherein the reaction is carried out at a pH range of from about pH 6.2 to about pH 6.5.

11. A method for preparing 3-amino-5-(t-butyl)-isoxazole which comprises reacting pivalyl acetonitrile with hydroxylamine in a solvent at a temperature in the range of from about room temperature to about the reflux temperature of the reaction mixture at a pH range of from about pH 6.0 to pH 7.0.

12. The method of claim 11 wherein the solvent is ethanol/water.

13. The method of claim 11 wherein the reaction is carried out at a pH range of from about pH 6.2 to about pH 6.5.

* * * * *